US008182150B2

(12) United States Patent
Gorges et al.

(10) Patent No.: US 8,182,150 B2
(45) Date of Patent: May 22, 2012

(54) CALIBRATION PROCEDURE FOR THE RELATIVE POSITION OF A TABLE AND C-ARM ON A MEDICAL IMAGING SYSTEM

(75) Inventors: Sebastien Gorges, Versailles (FR); Yves Lucien Trousset, Palaiseau (FR)

(73) Assignee: General Electric Company, Schenectady, NY (US)

( * ) Notice: Subject to any disclaimer, the term of this patent is extended or adjusted under 35 U.S.C. 154(b) by 196 days.

(21) Appl. No.: 12/704,321

(22) Filed: Feb. 11, 2010

(65) Prior Publication Data

US 2010/0204562 A1 Aug. 12, 2010

(30) Foreign Application Priority Data

Feb. 12, 2009 (FR) ...................................... 09 50899

(51) Int. Cl.
*G01D 18/00* (2006.01)
(52) U.S. Cl. ........................................ 378/207; 378/205
(58) Field of Classification Search .................. 378/207, 378/205, 208, 209
See application file for complete search history.

(56) References Cited

U.S. PATENT DOCUMENTS

2004/0202288 A1* 10/2004 Pescatore et al. ............. 378/207

FOREIGN PATENT DOCUMENTS

WO 2005/041835 A2 5/2005

OTHER PUBLICATIONS

Gorges S et al: "An effective technique for calibrating the intrinsic parameters of a vascular C-arm from a planar target" Progress in Biomedical Optics and Imaging—Proceedings of SPIE—Medical Imaging 2006: Visualization, Image-Guided Procedures, and Display 2006 SPIE US, vol. 6141, 2006, XP002539771; p. 2, Paragraph 4—p. 6, paragraph 6.
Gorges S et al: "Model of Vascular C-Arm for 3D Augmented Fluoroscopy in Interventional Radiology" Medical Image Computing and Computer-Assisted Intervention—MIC CAI 2005 Lecture Notes in Computer Science; LNCS, Springer, Berlin, DE, vol. 3750, Jan. 1, 2005; pp. 214-222, XP019021757, ISBN: 978-3-540-29326-2, p. 215, paragraph 2—p. 220, paragraph 1.

\* cited by examiner

*Primary Examiner* — Hoon Song
(74) *Attorney, Agent, or Firm* — Global Patent Operation; Jonathan E. Thomas

(57) ABSTRACT

A method of calibrating a mechanical model of behavior and movement of an interventional radiology table by moving the table over at least one degree of freedom, acquiring at least one set of images corresponding to different positions of the table and C-arm, obtaining at least one set of images of a test object from different positions, using the images of the test object to determine parameters of the mechanical model of table behavior and movement, and combining these parameters with data given by table movement sensors so as to deduce the true relative positions of the table with respect to the medical imaging system.

5 Claims, 1 Drawing Sheet

| Acquisition of sets of images (Im−max, Im−0, Im+max) for different simple movements |
|---|

| Determination of a movement vector taking into account extrinsic play take-up |
|---|

| Non-linear optimisation |
|---|

CALIBRATION PROCEDURE FOR THE RELATIVE POSITION OF A TABLE AND C-ARM ON A MEDICAL IMAGING SYSTEM

CROSS-REFERENCE TO RELATED APPLICATIONS

This application claims priority under 35 U.S.C. §§119(a)-(d) or (f) to prior-filed, co-pending French patent application number 0950899, filed on Feb. 12, 2009, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

This invention relates to a method and a device for medical imaging, and more specifically, calibration of the mechanical model for the behavior and movement of a radiology examination table in relation to a vascular gantry in medical imaging systems.

2. Description of Related Art

Vascular gantries are typically used in medical imaging in order to acquire: first, prior to an operation, 3-D images of a given organ; and second, in the course of the operation, 2-D fluoroscope images of the same organ.

This type of 2-D fluoroscopic image makes it possible, for example, for the surgeon to get oriented before navigating around the vascular structures, and to verify the position and deployment of his tools.

In the technique known as 3-D Augmented Fluoroscopy (3DAF), the 3-D image obtained in the course of the operation is superimposed on the 2-D image of the structure or the organ being operated on, acquired prior to the operation. The 3-D view is calculated in such a way as to give it the same viewing angle as the 2-D fluoroscopic on which it is being superimposed.

This kind of superimposing assumes whatever exact knowledge of the relative position and the distortion undergone by the table carrying the object or the patient and the vascular gantry carrying the source and the imaging system sensor.

An example of a process that allows for calculating the position and distortions undergone by the vascular gantry is described in patent application US 2007/0172033. This document describes how to calibrate the mechanical model of the vascular gantry which will then be used jointly with the system positioning sensors in order to recalibrate the relative positions of the 3-D image and the fluoroscopic images (making it possible to generate "augmented fluoroscopic images").

However, the table's movement and the distortion it undergoes are not taken into account in this calibration method.

One difficulty lies in calculating the table's parameters with regards to its movements and mechanical behavior. The greater the precision with which the table's mechanical parameters are determined, the better will be the quality of the recalibrated augmented fluoroscopic images.

BRIEF SUMMARY OF THE INVENTION

The present invention proposes a calibration procedure for the table's mechanical model that will help to overcome these limitations. Most notably, the proposed procedure makes it possible to determine the table's mechanical parameters using a limited number of calibration positions.

More specifically, the present invention proposes a calibration procedure for a mechanical model of behavior and movement of a radiology examination table that moves in relationship to a vascular gantry medical imaging system, using a phantom target positioned on the table.

The table moves with at least one degree of play, and at least one set of images is acquired that corresponds to the various positions of the table and to the degree of play in question. We can determine from the images obtained of the target, the various parameter positions of the mechanical model of behavior and movement of the table.

These parameters are then combined with the information provided by the table's positioning sensors in order to infer the table's true relative positions in relationship to the medical imaging system.

This mechanical model, coupled with information provided by the table positioning sensors can then be used, among other things, in augmented fluoroscopic applications in order to precisely determine the table's movements and provide optimum recalibration of the 3-D image and the fluoroscopic image.

Notably, for at least one set of images acquired for a basic degree of play, we can detect, in the images obtained in this manner, the positioning of the phantom's elements. For at least two images, one corresponding to the reference position and the other to the acquisition position for the set of images, we can infer a projection matrix as well as the extrinsic parameters, we can determine the calculated shift of the table by combining the inferred extrinsic parameters of the reference position with those of the other acquisition position. We can determine from this calculated movement and the movement measured by the system's sensors, a basic shift vector specific to the degree of play corresponding to the image set. These steps are used for example for various image sets acquired by the shift of a basic degree of play, and are used in determining an average basic vector of shift, based on the various specified basic vectors.

In addition, they may be utilized for image sets acquired by various degrees of basic play. Moreover, a nonlinear optimization system can be used in order to calculate all of the acquired image sets. The invention also proposes a medical imaging system comprising a radiology examination table and a vascular gantry suitable for processing this type of calibration.

BRIEF DESCRIPTION OF THE SEVERAL VIEWS OF THE DRAWINGS

Additional characteristics and advantages of the present invention will be described below, in a way that is meant to be indicative and non-limiting, and should be considered taking into account the figures contained in the following appendices.

DETAILED DESCRIPTION OF THE INVENTION

Overview

Figures 1, 2:
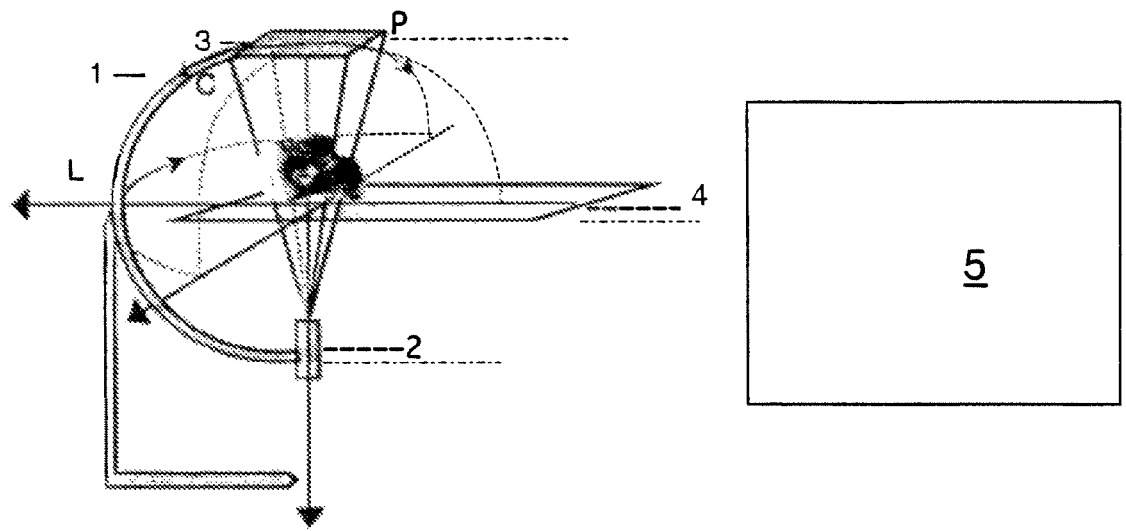
FIG. 1 is a schematic representation of a medical imaging system corresponding to one possible method of implementing the invention.
FIG. 2 is a block diagram showing the various steps of a calibration procedure.

The medical imaging system shown in FIG. 1 comprises (1) a C-Arm (vascular gantry) carrying (2) a radiation source at one end (for example x-rays) and (3) a sensor at the other end.

Conventionally, the C-Arm can be swiveled around the axis of a table 4 designed to carry the patient being imaged and can be moved around said table 4 in various movements L, P, C, designated by the double arrows in the figure, in such a way as to adjust the positioning of said arm in relation to the part of the patient undergoing imaging.

Note that, movement L corresponds to the C-Arm's horizontal movement (swinging movement around the axis going by source 2 and sensor 3); movement C corresponds to the C-Arm moving around its own axis, on its own plane; movement P corresponds to the C-Arm's movement around the table's main axis.

For the various movements, the centered positions as represented in FIG. 1 are designated by O.

Source 2, for example, is an x-ray source. It radiates conically and the radiation is picked up by sensor 3 after going through the patient undergoing the imaging. Sensor 3 is of the matrix type and for this purpose possesses a detector matrix.

The signals sent from the detectors of the matrix are then digitalized, and a processing unit 5 receives, processes, and where applicable, memorizes the resulting 2-D digital images. Before and after processing, the resulting 2-D digital images may also be memorized independently of processing unit 5, and for this purpose any type of media may be used: CD-ROM, USB drive, central server etc.

Conventionally, it is possible for example to carry out prior acquisition of a set of 2-D images of the organ to be examined, by having the C-Arm orbit around the patient. The resulting set of 2-D images is then processed in order to generate a 3-D image of the organ that is to be imaged. The procedures for isolating a given organ and determining a 3-D image from a set of 2-D images are well known.

The 3-D image is then displayed from a given angle, with the 3-D image points corresponding to the X and Y coordinates in the plane perpendicular to the angle from which view Z was shot, being projected in accordance with their depth along that direction.

The 3-D image can, for example, be displayed in superimposition over a 2-D image, for example a fluoroscopic image acquired in real-time in the course of an operation. An example of this type of processing is described in the scientific article "Model of a Vascular C-Arm For 3-D Augmented Fluoroscopy in Interventional Radiology", Sebastien Gorges et al, which was presented at the International MICCAI 2005 conference in Palm Springs, USA.

Calibration

Mechanical Model of the Table

The goal of the calibration is to determine the mechanical parameters of table 4 from a set of x-ray images of a phantom target placed on the table, with the images having been shot using different table positions. The mechanical model of table 4 is made up of parameters that model the movements of table 4 and its distortions. In the rest of the description, a simple model of table 4 is considered, comprising transfer movements only.

$$\vec{v}\_la = [x_{la}, y_{la}, z_{la}]^t \vec{v}\_lo = [x_{lo}, y_{lo}, z_{lo}]^t \vec{v}\_h = [x_h, y_h, z_h]^t| \quad \text{(Equation 1)}$$

are the vectors that represent the three directions of the table 4 in the process of being determined.

Naturally, the simplified model described here is intended only as at non-limiting example.

Note

In the subsequent text, the following notation is used:

$$\vec{x}\_la = [x_{la}, y_{la}, z_{la}]^t \vec{v}\_lo = [x_{lo}, y_{lo}, z_{lo}]^t \vec{v}\_h = [x_h, y_h, z_h]^t| \quad \text{(Equation 2)}$$

as direction vectors of the table's transfer movements.

d_la, d_h are measurements of the table 4's movements (for example, in ⅒ mm) generated from external sensors making it possible to measure the movements of table 4 with relationship to a reference position.

For a given orientation of the vascular gantry and a focal length, the definition consists of +max, −max, and 'centered', on the following table 4 positions:
1. centered: is the position of table 4 when the helix is iso-centered
2. −max: maximum transfer movement that may be applied while maintaining the image of the helix in the x-ray image
3. +max: symmetrical transfer movement.

In addition, in the rest of the text, M=K*E designates the image projection matrix of an object positioned on table 4 in a given relative position of table 4 and the vascular gantry, where K is the matrix of the intrinsic parameters that take into account the internal geometry of the vascular gantry, and where E is the matrix of the extrinsic parameters that describe table 4's and the gantry's relative positioning. A description of the projection matrix parameters can be found in the article "Multiple View Geometry In Computer Vision", Richard Hartley and Andrew Zisserman, Cambridge Press University, June 2000.

The matrix K of the intrinsic parameters correspond to the projection parameters of source 2 from sensor 3.

The matrix E of the extrinsic parameters depends on the position of C-gantry in relation to the table.

Acquisition Prior to Calibration

In order to determine the parameters of table 4's mechanical model for various positions of table 4, we acquire a certain number of images from a phantom helix that is positioned on table 4.

For example, sets of three or five x-ray images are acquired for the various positions of the C-Arm and the following movements:
  position of the C-Arm such that L=P=C=0 with the table being moved according to v_la,
  position of the C-Arm such that L=0 (with the plane of the C-Arm being perpendicular to the table's axis) and P=C=O, the table being moved according to v_lo,
  position of the C-Arm such that L=0 (with the plane of the C-Arm being perpendicular to the table's axis) and P=C=O, with the table being moved according to v_h
  position of the C-Arm such that L=0 (with the plane of the C-Arm being perpendicular to the table's axis), P=O, C=90 (with the C-Arm swiveling on its own axis), and the table being moved according to v_h,
  position of the C-Arm such that L=O (with the plane of the C-Arm being perpendicular to the table's axis), P=O, C=90 (with the C-Arm swiveling on its own axis), and the table being moved according to v_lat.

Calibration Processing

Once the various image sets have been acquired, calibration is carried out in the following manner:

In this description the goal is to determine the transfer vectors for table 4 representing the three degrees of play, namely:

$$\vec{v}\_la \; \vec{v}\_lo \; \vec{v}\_h| \quad \text{(Equation 3)}$$

First Step

For each set of images, we detect for the image processing the 2D positioning of the calibration target points in the x-ray images that were obtained.

Following this, a method is used in order to determine the M_i projection matrix as well as the K_i and E_i matrices of the intrinsic parameters and extrinsic parameters corresponding to each of the images i of the set of positions, with M_i=K_iE_i.

The calculation carried out for this purpose is for example determined by unit 5.

Such a method is described for example in *Vision par Ordinateur* (*Using the Computer as a Vision Tool*) by Radu Horaud and Olivier Monga, chapter 5; "An Optimal Solution For Mobile Camera Calibration", by Puget and Skorda, ECCV 1990; and "*Geometrical Calibration For 3D X-Ray Imaging*", by Rougé, Picard, Trousset et Ponchut, SPIE 1993-161-169.

Second Step: Initialization of the Table Model

For each set of images corresponding to a single movement of the table (i.e. image sets named v_la, v_lo, and v_h set) we will determine in linear fashion the table's transfer movement vectors.

For this purpose, for each image set, we carry out the following processing:

We determine table 4's single (simple) movements by combining the extrinsic parameters E_ref taken from a reference position and the intrinsic parameters E_i of any position, determined in step 1.

Movement D of table 4 between the two positions can now be given by:

$$D = E^{-1}\_i \, E\_\text{ref} = [R|T] = [Id|T] \quad \text{(Equation 4)}$$

where R is equal to the identity if the table 4 is not rotated.

Since we also know the length of the movement effectively measured by the system's sensors between position i and the reference position ref, we infer that table 4's movement $\bar{v}|$ corresponds to the image set being processed.

$$D = T = d^*\bar{v}| \text{ that is } \bar{v}| = T/d \quad \text{(Equation 5)}$$

where d is the movement of table 4 measured by the system sensors.

On the basis of several successive determinations and on the basis of several reference points selected in the image set being processed, we calculate a mean value for this movement vector Third Step In order to improve the precision of this estimation, we optimize, in non-linear fashion, a criterion C that verifies acquired x-ray images in all positions:

$$\left[ \vec{v}\_la \; \vec{v}\_lo \; \vec{v}\_h \right] = \text{argmin}(C)| \quad \text{(Equation 6)}$$

with $C = \sum_j^N \sum_i^K \left\| q_{ij} - M_j X_i \right\|$ (Equation 7)

Where q_ij is the $i^{th}$ target point detected in image j, M_j is the projection matrix constructed from data from the model of table 4 as well as table 4's position sensors, and Xi is the $i^{th}$ 3D calibration target point. In our example, the table 4 model is made up solely of transfer vectors, in such a way that Mj is given by:

$$M_j = M_{ref} * \begin{bmatrix} 1 & 0 & 0 & transx \\ 0 & 1 & 0 & transy \\ 0 & 0 & 1 & transz \\ 0 & 0 & 0 & 1 \end{bmatrix} \quad \text{(Equation 8)}$$

Where transx, transy and transz are given by:

$$\begin{bmatrix} transx \\ transy \\ transz \end{bmatrix} = \begin{bmatrix} \vec{v}\_la & \vec{v}\_lo & \vec{v}\_h \end{bmatrix} * \begin{bmatrix} d\_la \\ d\_lo \\ d\_h \end{bmatrix} \quad \text{(Equation 9)}$$

With dla, dlo and dh, the length of the transfer generated by the transfer sensors in relationship to the reference position respectively for the lateral, longitudinal and height axes.

$$\vec{v}\_la = [x_{la}, y_{la}, z_{la}]^t \; \vec{v}\_lo = [x_{lo}, y_{lo}, z_{lo}]^t \; \vec{v}\_h = [x_h, y_h, z_h]^t| \quad \text{(Equation 10)}$$

the transfer movement vectors are found.

When the transfer movement vectors ($\vec{v}\_la \; \vec{v}\_lo \; \vec{v}\_h$)| have been established, we possess precise knowledge of the table's basic movement axes (in the present case, its transfer movement directions). This information is taken into account by unit 5 when it calculates table 4's true position. Unit 5 calculates the true position by combining the vectors from the basic movements with the controlled movement for table 4.

The transfer vectors thus determined are used in applications in order to calculate the new projection matrix Mj taking into account the table's movement. The table vectors and the position sensor values (in accordance with the above equation referenced eq 1) are combined in order to determine the new matrix. The new matrix can then be used in augmented fluoroscopy applications to help in guiding tools.

What is claimed is:

1. A method to calibrate a mechanical model of behaviour and movement of an interventional radiology table, the method comprising the steps of:
   moving the table over at least one degree of freedom;
   acquiring at least one set of images corresponding to different positions of the table and C-arm;
   obtaining at least one set of images of a test object from different positions;
   using the images of the test object to determine parameters of the mechanical model of table behaviour and movement;
   combining these parameters with data given by table movement sensors so as to deduce the true relative positions of the table with respect to the medical imaging system; and acquiring images for an elementary degree of freedom, wherein:
in the images thus obtained, the positioning of elements of the test object is detected:
a matrix of projection parameters is derived therefrom for at least two images, one thereof corresponding to a reference position and the other to another acquisition position of the set of images, from which extrinsic parameters are deduced;
a calculated movement of the table is determined by combining the extrinsic parameters determined for the reference position and for the other acquisition position; and
from this calculated movement and the movement measured by the system's sensors, an elementary movement vector is determined associated with the elementary degree of freedom to which the set of images corresponds.

2. The method according to claim 1, wherein the step of acquiring images for an elementary degree of freedom is implemented for different images of a set acquired by movement over one degree of freedom, and a mean elementary movement vector is determined in relation to the different elementary vectors determined.

3. The method according to claim 1, wherein the step of acquiring images for an elementary degree of freedom is implemented for sets of images acquired for different degrees of freedom.

4. The method according to claim 1, further comprises the step of performing a non-linear optimisation processing, calculated on all the acquired sets of images.

5. A medical imaging system, the system comprising:
an interventional radiology table;
a vascular C-arm; and
processing means, wherein:
the processing means calibrates a mechanical model of behaviour and movement of an interventional radiology table by:
moving the table over at least one degree of freedom;
acquiring at least one set of images corresponding to different positions of the table and C-arm;
obtaining at least one set of images of a test object from different positions;
using the images of the test object to determine parameters of the mechanical model of table behaviour and movement;
combining these parameters with data given by table movement sensors so as to deduce the true relative positions of the table with respect to the medical imaging system; and
acquiring images for an elementary degree of freedom wherein:
in the images thus obtained, the positioning of elements of the test object is detected;
a matrix of projection parameters is derived therefrom for at least two images, one thereof corresponding to a reference position and the other to another acquisition position of the set of images, from which extrinsic parameters are deduced;
a calculated movement of the table is determined by combining the extrinsic parameters determined for the reference position and for the other acquisition position; and
from this calculated movement and the movement measured by the system's sensors, an elementary movement vector is determined associated with the elementary degree of freedom to which the set of images corresponds.

\* \* \* \* \*

UNITED STATES PATENT AND TRADEMARK OFFICE
CERTIFICATE OF CORRECTION

PATENT NO. : 8,182,150 B2  
APPLICATION NO. : 12/704321  
DATED : May 22, 2012  
INVENTOR(S) : Gorges et al.

Page 1 of 1

It is certified that error appears in the above-identified patent and that said Letters Patent is hereby corrected as shown below:

In Column 4, Line 15, in Equation 2, delete "$\vec{x}\_{la}=$," and insert -- $\vec{v}\_{la}=$ --, therefor.

In Column 4, Line 18, delete "d_la," and insert -- d_lo, d_la, --, therefor.

In Column 5, Line 58, after "vector" insert -- $\vec{v}_{l\ast}$ --.

In Column 6, Line 29, delete "dla, dlo and dh," and insert -- d_la, d_lo and d_h, --, therefor.

In Column 7, Line 4, in Claim 1, delete "detected:" and insert -- detected; --, therefor.

In Column 8, Lines 16-17, in Claim 5, delete "freedom" and insert -- freedom, --, therefor.

Signed and Sealed this  
Twentieth Day of November, 2012

David J. Kappos  
*Director of the United States Patent and Trademark Office*